United States Patent [19]

Madsen et al.

[11] Patent Number: 4,898,879

[45] Date of Patent: Feb. 6, 1990

[54] NURTITIONAL COMPOSITION FOR MANAGEMENT OF HEPATIC FAILURE

[75] Inventors: David C. Madsen, Libertyville; Hugh N. Tucker, Chicago, both of Ill.

[73] Assignee: Baxter International Inc., Deerfield, Ill.

[21] Appl. No.: 208,805

[22] Filed: Jun. 17, 1988

Related U.S. Application Data

[63] Continuation of Ser. No. 935,887, Mar. 9, 1987, abandoned, which is a continuation of Ser. No. 805,394, Dec. 3, 1985, abandoned, which is a continuation of Ser. No. 479,104, Mar. 28, 1983, abandoned, which is a continuation of Ser. No. 278,914, Jun. 29, 1981, abandoned.

[51] Int. Cl.$^4$ ................. A61K 31/195; A61K 31/415
[52] U.S. Cl. .................................... 514/400; 514/561
[58] Field of Search .............................. 514/400, 561

[56] References Cited

U.S. PATENT DOCUMENTS 3,697,287  7/1984  Wintz ........................................ 95/1
3,950,529  4/1976  Fischer et al. ...................... 514/400

OTHER PUBLICATIONS

Dickerson, "Nutritional Support Update" American Druggest, Oct. 1985, pp. 144–149.
Nance et al., "Eck's Fistula Encephalopathy in Germ Free Dogs", Ann. Surg. vol. 174 (5) 856–862 (11/71).
Ghadimi, "Acid–Base Problens After Intravenous Amino Acids", New Eng. J. Med. vol. 288 (8): 420–421 (1973).
Greenburger et al., "Effect of Vegetable and Animal Protein Diets in Chromic Hepatic Encephalopathy", Am. J. Dig. Div. vol. 22 (10): 845–855 (1977).
Zieve, "Amino Acid in Liver Failure", Gastroenterology, vol. 26 No 1 219–221 (01/79).
Zieve, "Pathogenesis of Hepatic Coma", 118 Arch. Inter Med. 211 (1966).
Fischer et al., "False Neurotransmitters and Hepatic Failure", The Lancet 75–79 (71).
Aguirre et al., "Plasma Amino Acids in Dogs with Two Expermental Forms of Liver Damage", J. of Sur. Res., vol. 16. No. 4, p. 339 (1974).
Fischer et al., "Plasma Amino Acids in Patients with Hepatic Encephalipathy", Am. J. Sur., vol. 127 p. 40 (1974).
Fischer et al., "The Effect of Normalization of Plasma Amino Acids on Hepatic Encephalopathy in Man", vol. 80, No. 1, p. 77–92 (07/76).
Rosen et al., "Plasma Amino Acid Patterns in Hepatic Encephalopathy of Differing Etiology", Gast., vol. 72 p. 483 (1977).
Maddrey et al., "Chronic Hepatic Encephalopathy", Mod. Cl. N. Amer., vol. 59, No. 4 p. 937 (1975).
Smith et al., "Alterations in Plasma CSF Amino Acids, Amines, and Meabolites in Hepatic Coma", Ann. Sur., vol. 187 No. 3, p. 343 (1978).
Iob et al., "Alterations in Plasma-Free Amino Acids in Dogs with Hepatic Insufficiency", Sur. p. 766 (05/70).
Ogihara et al., "Tryptohan as Cause of Hepatic Coma", New Eng. J. of Med., vol. 275, No. 22, p. 1255 (1966).
Wu et al., "Changes in Free Amino Acids in the Plasma During Hepatic Coma", p. 845 (1955).
Iber et al., "The Plasma Amino Acids in Patients with Liver Failure", J. Lab. & Clin. p. 417 (1957).
Mattson et al., "Alterations in Individual Free Amino Acids in Brain During Acute Hepatic Coma", Surgery p. 263 (1970).
Vinnars et al., "The Nutrition Effect in Man of Non-Essential Amino Acids Infused Intravenously Together with the Essential Ones", Acta. anesth, Scandina., vol. 14, pp. 259–271 (1970).
Hirayama, "Trypotophan Metabolism in Liver Disease", Clinica Chmica Acta 32 p. 191 (1971).
Rudman et al., "Obersations in Nitrogen Metabolism of Patients with Portue Ciffhosis", A. J. Clin, Nut., vol. 23, p. 1203 (09/70).
Levine et al., "Tyrosine Metabolism in Patients with Liver Disease", J. Clin. Inv., vol. 46, p. 2012 (1967).
Rose, "Amino Acid Requirements in Man", Federation Proceedings p. 546.
Perez–Cruet et al., "Dietary Regulation of Brain Tryophan Metabolism by Plasma Ratio of Free Tryophan and Neutral Amino Acids in Humans", Nature, vol. 248, p. 693 (1976).

*Primary Examiner*—Stanley J. Friedman
*Attorney, Agent, or Firm*—Susan Bennett Fentress; Robert E. Hartenberger; Paul C. Flattery

[57] ABSTRACT

Nutritional compositions for management of hepatic failure are improved by eliminating certain ammonotelic amino acids and reducing the proportion of essential ammonotelic amino acids. A composition is provided which is optimized for nutritional therapy and suppression of hyperammonemia.

22 Claims, No Drawings

NURTITIONAL COMPOSITION FOR MANAGEMENT OF HEPATIC FAILURE

The present application is a continuation of U.S. patent application No. 935,807 filed Mar. 9, 1987, which is a continuation of U.S. patent application No. 805,394 filed Dec. 3, 1985, which is a continuation of U.S. patent application No. 479,104 filed Mar. 28, 1983 and which is a continuation of U.S. patent application No. 278,914 filed June 29, 1981 all are abandoned.

BACKGROUND OF THE INVENTION

This invention relates to compositions and methods for nutritional management of hepatic (liver) failure. In particular the invention is directed at novel amino acid compositions designed to meet the altered metabolic needs of patients suffering from hepatic failure and the attendant derangements of normal amino acid metabolism characterized by this clinical condition.

Hepatic failure has numerous potential causes. Included among these causes are traumatic injuries to the organ and metabolic causes of a chronic (e.g., alcoholism) or acute nature (e.g., hepatitis, sepsis).

Of the numerous functions performed by the liver, one in particular has importance as the subject of the invention described below. The liver is the site of detoxification of numerous substances, in particular those nitrogenous wastes associated with protein metabolism. Especially important is the toxic by-product, ammonia ($NH_3$). The liver normally will detoxify ammonia by forming the nitrogen-containing substance urea (ureagenesis), which is then excreted via the kidneys.

When the liver is in various degrees of failure its ability to detoxify ammonia can become compromised. As a result ammonia can accumulate in the blood (hyperammonemia). It is a widely accepted belief among clinicians and researchers that hyperammonemia is dangerous, since ammonia is believed to be extremely toxic to the brain. A potential result of hyperammonemia is the onset or deepening of coma. When such coma is associated with hepatic failure it is termed "hepatic coma" or "hepatic encephalopathy".

Although the exact or immediate cause(s) of hepatic coma are not known with certainty, it is widely believed that ammonia can be a contributory factor. This is reflected in the fact that some of the non-nutritional therapeutic modalities employed in the clinical management of hepatic failure include treatments which have as their goal the reduction or elimination of ammonia input into the patient. Specifically, administration of the antibiotic, neomycin, and the synthetic carbohydrate, lactulose, are directed at reducing the production of ammonia by intestinal bacteria. It is known that the intestinal bacteria are the source of a substantial amount of ammonia, which reaches the blood-stream by intestinal absorption. Neomycin and lactulose are administered to reduce or eliminate this source of ammonia.

Current therapies for hepatic failure, with or without the complication of coma, are not generally nutritional in nature.

However, nutritional compositions which are disclosed to be tailored for hepatic failure are known. For example, see Ghadimi, U.S. Pat. No. 3,832,405, Fischer et al, U.S. Pat. No. 3,950,529 and West German Offenlegungsschrift 26 36 828.

It is known that certain amino acids (the L-forms of threonine, serine, tryptophan, glutamine, histidine, and glycine, hereafter termed "ammonotelic" amino acids) are catabolized by the body with the release of ammonia.

It is an object of this invention to supply an amino acid composition which will reduce the ammonia produced endogenously (by the body, rather than by bacterial floria) by reducing the proportion of ammonotelic amino acids present in the nutritional source.

It is another object to ameliorate the hyperammonemia which accompanies hepatic dysfunction, thereby reducing the likihood of a lapse into hepatic coma or a deepening of the comotase state.

It is an additional object to provide adequate nutrition to the hepatic diseased patient without compromising the foregoing two objects.

These and other objects will become apparent from the specification as a whole.

SUMMARY OF THE INVENTION

We have discovered that the proportion of ammonotelic amino acids to other essential and nonessential amino acids must be carefully balanced. We believe that this proportion is critical to the successful therapy of the hepatic failure patient. Sufficient essential ammonotelic amino acids must be present to provide the required nutrients, but an excess of ammonotelic amino acids will exacerbate the clinical syndromes associated with liver disease, in particular hyperammonemia. Thus it is important that the proportion of ammonotelic amino acids not be reduced to a level at which nutrition is comprised, but that the level be sufficiently low as to not unnecessarily contribute to hyperammonemia. This is most readily accomplished by severely reducing or by eliminating L-serine, L-glycine and L-glutamine from mixtures of essential and nonessential amino acids to be used for nutritional support of liver diseased patients. The essential or semi-essential ammontelic amino acids histidine, threonine and tryptophan are reduced to the lowest proportion compatible with effective nutritional support. The proportion of ammonotelic amino acids meeting these requirements has been found to be about from 8 to 16 mole percent of the total amino acid composition.

DETAILED DESCRIPTION OF THE INVENTION

The compositions of this invention will contain the essential amino acids L-leucine, L-isoleucine, L-valine, L-lysine, L-threonine, L-methionine, L-phenylalanine and L-tryptophan. They may also contain the nonessential amino acids L-tyrosine, L-arginine, L-proline, L-alanine and glycine. L-histidine is considered semi-essential, and in fact may be essential for neonates. For the purposes of nutrition in liver disease and this application, histidine will be denominated an essential amino acid.

L-serine and L-glutamine are the ammonotelic amino acids which are most readily absent from the compositions of this invention, even though serine has heretofore been included as a required amino acid in certain prior art nutritional amino acid compositions for liver disease, e.g., those of Fisher et al, U.S. Pat. No. 3,950,529. Glycine is generally reduced to a low proportion of the total amino acids, ordinarily less than about 8 mole % and preferably about from 2 to 6 mole %. Glycine may be entirely absent from the compositions of this invention, but this is not preferred.

The essential ammonotelic amino acids histidine, threonine, and tryptophan are present in a proportion of about from 6 to 16 mole %, ordinarily about from 6 to 10 mole % and preferrably about 8 mole %. They are not entirely eliminated from the composition as this would be incompatible with the balanced nutritional objectives of the compositions described herein.

A typical composition of this invention will contain amino acids in the following proportions:

| Amino Acids | Mole Percent about from |
|---|---|
| L-leucine | 19.4 to 19.8 |
| L-isoleucine | 16.2 to 16.4 |
| L-valine | 14.5 to 14.8 |
| L-lysine | 10.2 to 10.3 |
| L-methionine | 1.1 to 1.2 |
| L-phenylalanine | 0.7 to 0.9 |
| L-threonine | 2.3 to 3.9 |
| L-tryptophan | 0.5 to 0.7 |
| L-histidine | 2.7 to 2.8 |
| L-arginine | 8.5 to 8.7 |
| L-proline | 8.1 to 8.3 |
| glycine | 5.6 to 5.8 |
| L-alanine | 8.1 to 8.3 |

The relative proportions of the amino acids in the above schedule may vary by as much as about 15% of the mole percent ranges given, although in the most satisfactory composition the ranges will vary by no more than about 5%.

The ratio of essential amino acids to nonessential amino acids by weight should range about from 5:1 to 1:1. The essential amino acids should compromise about from 60 to 75% by weight of the total amino acids in the composition.

The aromatic amino acids L-phenylalanine, L-tyrosine and L-tryptophan are ordinarily present at less than about 8 mole %, preferrably less than 3 mole % and optimally about from 1 to 3 mole %.

The branched chain amino acids L-leucine, L-isoleucine and L-valine are present in a total of about from 40–55% of the composition by weight, and preferrably about 50% by weight.

Cysteine is not included in the compositions of this invention since it has been found, contrary to the teachings of Ghadami (U.S. Pat. No. 3,832,465), that the sulfur requirements of hepatic-diseased patients may be met by supplying L-methionine.

Whether the amino acid composition is administered parenterally or enterally will depend upon the clinical condition of the patient. If the gastrointestinal tract is sound the preferred administration route is enteral. Severely comatose patients will generally be fed parenterally. In non-comatose patients the composition may be administered as a supplement to normal oral nutrition. The suitable mode of administration will be within the skill of the ordinary artisan.

The composition may be supplemented with other nutrients such as vitamins, minerals, and biologically available, assimilable carbohydrates and fats. Supplementation may occur concomitant with administration by premixing the additional nutrients with the amino acids and then administering, or by simultaneously supplying the nutrients by a separate administration route.

Parenteral compositions will ordinarily contain monosaccharides such as dextrose at typical infusion concentrations, e.g., about from 10 to 40 percent by weight. Other carbohydrates such as oligosaccharides will be satisfactory. The solutions will be sterile and may contain stabilizers such as malate or sodium bisulfite. The concentration of amino acids in solutions for parenteral administration may range about from 1 to 10 grams/dl, and preferably is about from 6 to 7 grams/dl. The concentration is not critical, although as recognized by those skilled in the art the osmolarity of the solution should be compatible with the administration route (central or peripheral venous), and excessive water should not be given as carrier for the nutrients if elimination is perceived by the clinician to be a problem.

The enteral compositions are formulated particularly to provide the total nutritional requirements of the patient. Thus the Recommended Daily Dietary Allowances for water and fat soluble vitamins, and for minerals are provided in a typical daily dosage of amino acids (about 1 g protein/day/kg of patient body weight) and calories (about 20 kcal/day/kg).

The composition and methods of this invention will be more fully understood by reference to the subsequent examples.

EXAMPLE 1

This contemplated example illustrates the use of an embodiment of the invention in an enteral feeding mode.

A 50 year old, 60 kg male with an exacerbation of hepatic failure due to acute cirrhosis of the liver from chronic alcohol ingestion, and with significant weight loss due to under-nutrition, exhibited protein intolerance, characterized in part by elevated serum ammonia values ($>100$ $\mu$g/dl). The patient had a history of episodes of coma.

The composition to be administered to this patient had the following approximate analysis:

|  | G/96 g PACKET | % (W/W) | KCAL/ PACKET | CALORIES AS % TOTAL |
|---|---|---|---|---|
| L-Amino Acids | 10.0 | 10.4 | 40 | 10.6 |
| Carbohydrate | 73.2 | 76.3 | 292.9 | 77.4 |
| Fat* | 5.0 | 5.3 | 45.4 | 12.0 |
| Total nitrogen: | Approximately 1.55 g/3.4 oz (96) packet | | | |
| Total calories: | Approximately 378/3.4 oz (96 g) packet (338 nonprotein calories) | | | |
| Osmolarity: | At the usual dilution of 1.1 kcal/ml, the approximate osmolarity is 550 mOsm/l (osmolality is 690 mOsm/kg water). | | | |

*Sunflower oil, medium chain triglycerides (fractionated coconut oil). Glucose oligosaccharides, sucrose.

We claim:

1. A composition for administration to a patient having liver disease, comprising a cysteine free mixture of nonessential and essential amino, having from 8 to 16 total mole % of the composition consisting of L-serine, L-histidine, L-threonine, L-tryptophan, L-glutamine and glycine taken together; said L-theronine contributing from about 2.3 to 3.9% of the total mole % of said composition.

2. The composition of claim 1 wherein the ratio of essential amino acids to nonessential amino acids by weight ranges about from 5:1 to 1:1.

3. The composition of claim 1 wherein the nonessential amino acids comprise greater than about 20% by weight of the total amino acids in the composition.

4. The composition of claim 1 wherein the mole % of L-serine, L-histidine, L-threonine, L-thryptophan, L- glutamine and glycine taken together ranges about from 10 to 15.

5. The composition of claim 2 wherein said mole % ranges about from 11 to 13.

6. The composition of claim 1 containing L-leucine, L-isoleucine and L-valine in a total of about 50% of the composition by weight.

7. The composition of claim 1 wherein the nonessential amino acids comprise about from 60 to 75% by weight of the total amino acids in the composition.

8. A method for nutritional management of hepatic failure in a patient comprising the administration of a cysteine free mixture of nonessential and essential amino acids, having from 8 to 16 total mole % of the composition consisting of L-serine, L-histidine, L-threonine, L-tryptophan, L-glutamine and glycine taken together; said L-theronine contributing from about 2.3 to 3.9% of the total mole % of said composition.

9. The method of claim 8 wherein the ratio of essential amino acids to nonessential amino acids by weight ranges about from 5:1 to 1:1.

10. The method of claim 8 wherein the nonessential amino acids comprise greater than about 20% by weight of the total amino acids in the composition.

11. The method of claim 8 wherein the mole % of L-serine, L-histidine, L-threonine, L-tryptophan, L-glutamine and glycine taken together ranges about from 10 to 15.

12. The method of claim 8 wherein said mole % ranges about from 11 to 13.

13. The method fo claim 8 containing L-leucine, L-isoleucine and L-valine in a total of about 50% of the composition by weight.

14. The method of claim 8 wherein the nonessential amino acids comprise about from 60 to 75% by weight of the total amino acids in the composition.

15. A composition for administration to a patient having liver disease, comprising a cysteine free mixture of essential and nonessential amino acids in the following proportions:

| Amino Acids | Mole Percent About From |
| --- | --- |
| L-Leucine | 19.4 to 19.8 |
| L-Isoleucine | 16.2 to 16.4 |
| L-Valine | 14.5 to 14.8 |
| L-Methionine | 1.1 to 1.2 |
| L-Phenylalanine | 0.7 to 0.9 |
| L-Threonine | 2.3 to 3.9 |
| L-Tryptophan | 0.5 to 0.7 |
| L-Histidine | 2.7 to 2.8 |
| L-Arginine | 8.5 to 8.7 |
| L-Proline | 8.1 to 8.3 |
| Glycine | 5.6 to 5.8 |
| L-Alanine | 8.1 to 8.3 |

16. The composition of claim 15 wherein the mole percentages of L-leucine, L-isoleucine, L-valine, L-lysine, L-methionine, L-phenylalanine, L-threonine, L-tryptophan, L-histidine, L-arginine, L-proline, glycine and L-alanine are, respectively, about 19.4, about 16.2, about 14.5, about 10.2, about 1.1, about 0.8, about 3.9, about 0.6, about 2.7, about 8.5, about 8.1, about 5.6, and about 8.1.

17. The composition of claim 15 further comprising vitamins, minerals, and digestively assimilable carbohydrates and fats.

18. The composition of claim 15 in aqueous solution at an amino acid concentration of about from 1 to 15 grams/dl.

19. A method of nutritional management of a patient with liver disease comprising enterally administering the composition of claim 14 to the patient.

20. The composition of claim 15 wherein the mole percentages of L-leucine, L-isoleucine, L-valine, L-lysine, L-methionine, L-phenylalanine, L-threonine, L-tryptophan, L-histidine, L-arginine, L-proline, glycine and L-alanine are, respectively about 19.8, about 16.4, about 14.8, bout 10.3, about 1.2, about 0.8, about 2.3, about 0.6, about 2.8, about 8.7, about 8.3, about 5.8, and about 8.3.

21. The composition of claim 20 in sterile aqueous solution at a concentration of about from 3 to 15 grams of amino acid/dl.

22. The composition of claim 20 which is essentially free of electrolytes.

* * * * *